(12) United States Patent
von Oepen et al.

(10) Patent No.: US 8,206,370 B2
(45) Date of Patent: Jun. 26, 2012

(54) DUAL LUMEN GUIDEWIRE SUPPORT CATHETER

(75) Inventors: Randolf von Oepen, Los Altos Hills, CA (US); James M. Jacobs, Mountain View, CA (US); Richard Newhauser, Redwood City, CA (US)

(73) Assignee: Abbott Laboratories, Abbott Park, IL (US)

(*) Notice: Subject to any disclaimer, the term of this patent is extended or adjusted under 35 U.S.C. 154(b) by 287 days.

(21) Appl. No.: 11/738,382

(22) Filed: Apr. 20, 2007

(65) Prior Publication Data

US 2007/0293846 A1 Dec. 20, 2007

Related U.S. Application Data

(60) Provisional application No. 60/793,781, filed on Apr. 21, 2006.

(51) Int. Cl.
*A61M 25/00* (2006.01)
*A61M 5/178* (2006.01)
*A61M 5/00* (2006.01)
*A61M 1/00* (2006.01)
*A61M 3/00* (2006.01)
*A61M 25/098* (2006.01)

(52) U.S. Cl. .............. 604/523; 604/164.01; 604/164.13; 604/264; 604/265; 604/27; 604/284; 604/43; 604/528; 604/529

(58) Field of Classification Search .............. 604/103.04, 604/523, 264, 529, 508, 93.01, 164.01, 164.13, 604/284, 528, 265, 27, 43, 48, 158, 160, 604/161
See application file for complete search history.

(56) References Cited

U.S. PATENT DOCUMENTS

| 4,405,313 | A | * | 9/1983 | Sisley et al. ..................... 604/43 |
| 4,624,381 | A | | 11/1986 | Friedrich |
| 4,832,681 | A | | 5/1989 | Lenck |
| 4,921,479 | A | * | 5/1990 | Grayzel ......................... 604/509 |
| 5,057,092 | A | | 10/1991 | Webster, Jr. |
| 5,139,496 | A | | 8/1992 | Hed |
| 5,180,366 | A | | 1/1993 | Woods |
| 5,195,978 | A | * | 3/1993 | Schiffer ......................... 604/161 |
| 5,250,069 | A | | 10/1993 | Nobuyoshi et al. |
| 5,320,605 | A | * | 6/1994 | Sahota ..................... 604/101.01 |

(Continued)

FOREIGN PATENT DOCUMENTS

EP 0 279 959 8/1988

(Continued)

OTHER PUBLICATIONS

U.S. Appl. No. 11/738,384, filed Apr. 20, 2007, Von Oepen.

(Continued)

*Primary Examiner* — Kevin C Sirmons
*Assistant Examiner* — Shefali Patel
(74) *Attorney, Agent, or Firm* — Workman Nydegger; Jonathan Feuchtwang

(57) ABSTRACT

A dual lumen guidewire support catheter for accurately crossing a chronic total occlusion in a vessel is disclosed. The dual lumen guidewire support catheter includes a first lumen portion and a second lumen portion sharing a common side and a common distal end. The first lumen portion can be a rapid exchange or over-the-wire portion, while the second lumen portion is an over the wire portion. One or both of the portions can include a discontinuity to enable removal of a guidewire following placement through or at an occlusion or lesion.

18 Claims, 5 Drawing Sheets

U.S. PATENT DOCUMENTS

| | | | |
|---|---|---|---|
| 5,324,255 A | 6/1994 | Passafaro et al. | |
| 5,378,237 A | 1/1995 | Boussignac et al. | |
| 5,380,273 A | 1/1995 | Dubrul et al. | |
| 5,385,563 A * | 1/1995 | Gross | 604/284 |
| 5,405,380 A | 4/1995 | Gianotti et al. | |
| 5,423,773 A | 6/1995 | Jimenez | |
| 5,437,288 A | 8/1995 | Schwartz et al. | |
| 5,443,454 A * | 8/1995 | Tanabe et al. | 604/264 |
| 5,454,795 A | 10/1995 | Samson | |
| 5,460,608 A | 10/1995 | Lodin et al. | |
| 5,507,751 A | 4/1996 | Goode et al. | |
| 5,647,846 A | 7/1997 | Berg et al. | |
| 5,662,622 A | 9/1997 | Gore et al. | |
| 5,702,439 A | 12/1997 | Keith et al. | |
| 5,709,658 A * | 1/1998 | Sirhan et al. | 604/103.04 |
| 5,720,735 A * | 2/1998 | Dorros | 604/284 |
| 5,855,563 A | 1/1999 | Kaplan et al. | |
| 5,906,606 A | 5/1999 | Chee et al. | |
| 5,951,517 A | 9/1999 | Lampropoulos et al. | |
| 6,017,324 A * | 1/2000 | Tu et al. | 604/103.07 |
| 6,022,309 A | 2/2000 | Celliers et al. | |
| 6,152,909 A | 11/2000 | Bagaoisan et al. | |
| 6,210,393 B1 | 4/2001 | Brisken | |
| 6,210,404 B1 | 4/2001 | Shadduck | |
| 6,217,503 B1 * | 4/2001 | Weinberger et al. | 600/3 |
| 6,221,100 B1 | 4/2001 | Strecker | |
| 6,241,744 B1 | 6/2001 | Imran et al. | |
| 6,261,273 B1 * | 7/2001 | Ruiz | 604/284 |
| 6,299,595 B1 * | 10/2001 | Dutta et al. | 604/96.01 |
| 6,327,505 B1 | 12/2001 | Medhkour et al. | |
| 6,398,772 B1 | 6/2002 | Bond et al. | |
| 6,398,791 B1 | 6/2002 | Que et al. | |
| 6,416,740 B1 | 7/2002 | Unger | |
| 6,440,161 B1 * | 8/2002 | Madrid et al. | 623/1.11 |
| 6,461,383 B1 | 10/2002 | Gesswein et al. | |
| 6,482,218 B1 | 11/2002 | Tran | |
| 6,579,246 B2 | 6/2003 | Jacobsen et al. | |
| 6,582,390 B1 | 6/2003 | Sanderson | |
| 6,629,952 B1 | 10/2003 | Chien et al. | |
| 6,652,508 B2 | 11/2003 | Griffin et al. | |
| 6,679,879 B2 | 1/2004 | Shadduck | |
| 6,682,502 B2 | 1/2004 | Bond et al. | |
| 6,790,170 B2 * | 9/2004 | Moody et al. | 600/3 |
| 6,849,077 B2 * | 2/2005 | Ricci | 606/108 |
| 6,869,416 B2 * | 3/2005 | Windheuser et al. | 604/164.05 |
| 6,942,680 B2 | 9/2005 | Grayzel et al. | |
| 6,962,604 B2 | 11/2005 | Hijlkema | |
| 7,044,933 B2 | 5/2006 | VanDiver et al. | |
| 7,329,223 B1 | 2/2008 | Ainsworth et al. | |
| 7,344,528 B1 | 3/2008 | Tu et al. | |
| 7,789,906 B2 | 9/2010 | Blank | |
| 2001/0008976 A1 | 7/2001 | Wang | |
| 2001/0031243 A1 | 10/2001 | Unger | |
| 2002/0022831 A1 | 2/2002 | O'Connor et al. | |
| 2002/0072710 A1 | 6/2002 | Stewart et al. | |
| 2002/0107473 A1 | 8/2002 | Bond et al. | |
| 2002/0123716 A1 | 9/2002 | VanDiver et al. | |
| 2002/0123738 A1 | 9/2002 | Jansen et al. | |
| 2003/0009157 A1 | 1/2003 | Levine et al. | |
| 2003/0055377 A1 | 3/2003 | Sirhan et al. | |
| 2003/0069522 A1 | 4/2003 | Jacobsen et al. | |
| 2003/0135261 A1 | 7/2003 | Kugler et al. | |
| 2003/0191449 A1 | 10/2003 | Nash et al. | |
| 2004/0044350 A1 | 3/2004 | Martin et al. | |
| 2004/0054322 A1 | 3/2004 | Vargas | |
| 2004/0054347 A1 | 3/2004 | Zadno-Azizi et al. | |
| 2004/0093044 A1 | 5/2004 | Rychnovsky et al. | |
| 2004/0098021 A1 | 5/2004 | Laguna | |
| 2004/0102821 A1 | 5/2004 | Kawata et al. | |
| 2004/0103516 A1 | 6/2004 | Bolduc et al. | |
| 2004/0220473 A1 * | 11/2004 | Lualdi | 600/435 |
| 2004/0225278 A1 * | 11/2004 | Poole et al. | 604/523 |
| 2004/0230204 A1 | 11/2004 | Wortley et al. | |
| 2005/0004522 A1 | 1/2005 | Katoh et al. | |
| 2005/0021004 A1 | 1/2005 | Cully et al. | |
| 2005/0182371 A1 | 8/2005 | Wagner et al. | |
| 2005/0209582 A1 | 9/2005 | Quinn et al. | |
| 2006/0085023 A1 | 4/2006 | Davies, Jr. et al. | |
| 2006/0190022 A1 | 8/2006 | Beyar et al. | |
| 2007/0060880 A1 | 3/2007 | Gregorich et al. | |
| 2007/0250149 A1 | 10/2007 | Von Oepen et al. | |
| 2007/0270779 A1 | 11/2007 | Jacobs | |
| 2007/0293821 A1 | 12/2007 | Yribarren | |
| 2007/0299392 A1 | 12/2007 | Beyar et al. | |
| 2008/0058722 A1 | 3/2008 | Von Oepen et al. | |
| 2008/0065014 A1 | 3/2008 | Von Oepen et al. | |

FOREIGN PATENT DOCUMENTS

| | | |
|---|---|---|
| EP | 0 596 635 | 5/1994 |
| EP | 0598635 | 5/1994 |
| EP | 0 916 359 | 5/1999 |
| EP | 1 475 120 | 11/2004 |
| EP | 1 607 119 | 12/2005 |
| GB | 2 143 920 | 2/1985 |
| WO | WO 88/08727 | 11/1988 |
| WO | WO 93/06780 | 4/1993 |
| WO | WO 96/07448 | 3/1996 |
| WO | WO 96/39205 | 12/1996 |
| WO | WO 97/23158 | 7/1997 |
| WO | WO 97/39690 | 10/1997 |
| WO | WO 99/15070 | 4/1999 |
| WO | WO 99/17826 | 4/1999 |
| WO | WO 99/21600 | 5/1999 |
| WO | WO 99/64098 | 12/1999 |
| WO | WO 00/03756 | 1/2000 |
| WO | WO 01/03762 | 1/2001 |
| WO | WO 01/07101 | 2/2001 |
| WO | WO 03/057060 | 7/2003 |
| WO | WO 03/105671 | 12/2003 |
| WO | WO 2004/064891 | 8/2004 |
| WO | WO 2004/096338 | 11/2004 |
| WO | WO 2006/002199 | 1/2006 |
| WO | WO 2006/058434 | 6/2006 |
| WO | WO 2006/122243 | 11/2006 |
| WO | PCT/US07/67237 | 4/2007 |
| WO | PCT/US07/67238 | 4/2007 |
| WO | PCT/US07/67239 | 4/2007 |
| WO | PCT/US07/67242 | 4/2007 |
| WO | PCT/US07/67243 | 4/2007 |
| WO | PCT/US07/67244 | 4/2007 |
| WO | WO 2007/124495 | 11/2007 |
| WO | WO 2007/124496 | 11/2007 |
| WO | WO 2007/124497 | 11/2007 |
| WO | WO 2007/124499 | 11/2007 |
| WO | WO 2007/124500 | 11/2007 |
| WO | WO 2007/124501 | 11/2007 |
| WO | WO 2007/143288 | 12/2007 |

OTHER PUBLICATIONS

U.S. Appl. No. 11/738,378, filed Apr. 20, 2007, Von Oepen.
U.S. Appl. No. 11/738,372, filed Apr. 20, 2007, Yribarren.
U.S. Appl. No. 11/738,368, filed Apr. 20, 2007, Jacobs.
U.S. Appl. No. 11/738,386, filed Apr. 20, 2007, Von Oepen.
U.S. Appl. No. 60/793,781, filed Apr. 21, 2006, Von Oepen.
U.S. Appl. No. 11/738,372, Mail Date Jun. 9, 2008, Office Action.
U.S. Appl. No. 11/738,372, Mail Date Sep. 15, 2008, Office Action.
U.S. Appl. No. 11/738,368, Mail Date Jan. 23, 2008, Office Action.
U.S. Appl. No. 11/738,368, Mail Date Sep. 16, 2008, Office Action.
U.S. Appl. No. 11/738,372, Mail Date Mar. 30, 2009, Office Action.
U.S. Appl. No. 11/738,368, Mail Date Jan. 27, 2009, Office Action.
U.S. Appl. No. 11/738,384, Mail Date Mar. 31, 2011, Notice of Allowance.
U.S. Appl. No. 11/738,386, Mail Date Sep. 28, 2009, Office Action.
U.S. Appl. No. 11/738,386, Mail Date Apr. 22, 2010, Office Action.
U.S. Appl. No. 11/738,368, Mail Date Sep. 3, 2009, Office Action.
U.S. Appl. No. 11/738,372, Mail Date Nov. 6, 2009, Office Action.
U.S. Appl. No. 11/738,372, Mail Date May 12, 2010, Office Action.
U.S. Appl. No. 11/738,378, Mail Date Sep. 2, 2009, Office Action.
U.S. Appl. No. 11/738,378, Mail Date May 12, 2010, Restriction Requirement.
U.S. Appl. No. 11/738,384, Mail Date Mar. 2, 2010, Restriction Requirement.
U.S. Appl. No. 11/738,384, Mail Date May 14, 2010, Office Action.
U.S. Appl. No. 11/738,384, Mail Date Jul. 20, 2011, Issue Notification.

U.S. Appl. No. 11/738,372, Mail Date Jul. 26, 2010, Office Action.
U.S. Appl. No. 11/738,378, Mail Date Aug. 17, 2010, Office Action.
U.S. Appl. No. 11/738,386, Mail Date Nov. 8, 2011, Office Action.
U.S. Appl. No. 11/738,384, Mail Date Oct. 27, 2010, Office Action.
U.S. Appl. No. 11/738,378, Mail Date Oct. 4, 2010, Advisory Action.
U.S. Appl. No. 11/738,378, Mail Date Nov. 26, 2010, Office Action.
U.S. Appl. No. 11/738,372, Mail Date Dec. 23, 2010, Notice of Allowance.
U.S. Appl. No. 11/738,368, mailed May 1, 2012, Notice of Allowance.

* cited by examiner

DUAL LUMEN GUIDEWIRE SUPPORT CATHETER

CROSS-REFERENCE TO RELATED APPLICATIONS

This application claims the benefit of the U.S. Provisional Patent Application No. 60/793,781, filed Apr. 21, 2006, and entitled "Medical Devices," which is incorporated herein by reference in its entirety.

BACKGROUND

1. Technology Field

The present invention generally relates to intravascular catheters. In particular, the present invention relates to a dual lumen guidewire support catheter that facilitates the accurate positioning and delivery of a guidewire for passing through a chronic total occlusion ("CTO") of a body vessel.

2. The Related Technology

A CTO is a severe narrowing of a blood vessel, such as a coronary vessel, that results in a complete or nearly complete occlusion of the primary vessel. CTOs are quite common in diseased coronary vessels and typically occur where plaque is formed in the vessel, gradually reducing the size of the lumen in the vessel until it becomes quite small and results in thrombus formation resulting in a stenosis forming a total occlusion. As the total occlusion becomes chronic, the stenosis or blockage generally has a tendency to continue to grow with fibrous end caps being formed at the proximal and distal ends of the occlusion. These fibrous end caps tend to be fairly tough but do have varying degrees of toughness.

Angioplasty and stent implantation procedures are commonly employed to treat CTOs or other stenoses that form within the vascular anatomy of a patient. During an angioplasty, or percutaneous transluminal coronary angioplasty ("PTCA") procedure, a guiding catheter is advanced through the vasculature of the patient to a desired point. A guidewire, positioned within a balloon catheter, is extended from a distal end of the guiding catheter into the patient's coronary artery until it penetrates and crosses a blockage to be dilated. The balloon catheter is then advanced through the guiding catheter and over the previously introduced guidewire, until it is properly positioned across the blockage. Once properly positioned, the balloon is inflated to a predetermined size such that the material causing the blockage is compressed against the arterial wall, thereby expanding the passageway of the artery. The balloon is subsequently deflated, blood flow resumes through the dilated artery, and the balloon catheter is removed.

In attempting to treat such chronic occlusions, there is a need to have guidewires which can extend through the stenoses forming the chronic occlusions so that various types of treatments can be performed. Heretofore attempts to place guidewires across such stenoses or blockages have resulted in the guidewires following fissures in the plaque and creating false lumens or with the guidewire being directed in such a manner so as to perforate the wall of the vessel causing a vessel dissection. In attempting to perform such a guidewire crossing, it often has been necessary to exchange the guidewire for a stiffer wire, which is time consuming.

One of the methods used in crossing a CTO is the parallel wire technique. The parallel wire technique uses a first wire to try and cross the CTO. Often, the first guidewire passes into a dissection plane, sub-intimal plane or likewise tracks out of the vessel true lumen, the physician leaves the initial guidewire in place and uses it as a reference point to assist in passing a second wire through the CTO and into the other side of the vessel true lumen. However, when the second guidewire is inserted within the lumen, it is likely that the second guidewire will follow the same path already forged by the first guidewire. It is very difficult to get back on to the proper track necessary for a crossing of the CTO once the second guidewire has passed into a dissection plane or other false lumen.

In light of the above discussion, a need exists in the art for a catheter capable of use with multiple guidewires employed in treating intravascular blockages. In particular, a catheter configuration is needed that alleviates problems occasioned by the advancement of the catheter along a first guidewire that has been directed outside of the vessel lumen. Any solution to the above need should increase the likelihood of a successful crossing of an intravascular blockage. Moreover, any proposed solution should be adaptable for use with a variety of catheter types and configurations.

BRIEF SUMMARY

The present invention has been developed in response to the above and other needs in the art. Briefly summarized, embodiments of the present invention are directed to a dual lumen guidewire support catheter that is specifically intended to improve CTO interventions. The catheter has at least two guidewire lumens, thereby making it useful as a tool to implement a successful crossing of a CTO. According to the present invention, each guidewire lumen is placed in association with the other over at least part of its length, however, the lengths, distal ends, and proximal ends, may vary in location. For example, in one embodiment, the distal ends of both lumens are adjacent; however, the proximal ends terminate in staggered axial positions. The proximal ends of the catheter have at least one access port through which the first lumen and/or the second lumen may be entered. This construction provides at least two advantages. The first advantage is that differentiation of the first and second guidewire lumens is made easier, and therefore, the two guidewires can be more easily controlled at the proximal end. Secondly, one lumen can be constructed with a rapid exchange design, making exchange of the guidewire and support catheter easier.

In an alternative embodiment of the present invention, one or both lumens may include a discontinuity in their wall, such as a slit or weakened portion, which makes removal of the lumen over a guidewire possible. This is advantageous because when in use, the lumen can provide support to the guidewire over the entire guidewire length, however, the lumen of the catheter can also be removed quickly from the guidewire by displacing the guidewire through the discontinuity without sacrificing guidewire position. The catheter of the present invention therefore provides the benefits of both an over the wire catheter and a rapid exchange catheter.

The present invention also relates to a method for using the dual lumen guidewire support catheter. The method includes attempting to access and cross a CTO with a first guidewire. If a false lumen, dissection plane or sub-intimal plane is accessed instead, then the first guidewire is left in place, and a first lumen of the catheter is tracked over the first guidewire. In one configuration this first lumen is a rapid exchange lumen.

Once the catheter is in place adjacent to the CTO, a second guidewire can be tracked through the second catheter lumen. By doing so, there is no need to steer the second guidewire into place and therefore the second guidewire tip can be left substantially straight thus maximizing the pushability of the second guidewire. The second guidewire can then access the CTO and be advanced across the CTO. When crossing is achieved, the second guidewire may be displaced from the second catheter lumen through the second lumen discontinuity. The catheter may then be removed over the first guidewire, or the catheter and first guidewire may be removed together.

In another embodiment, the catheter includes a catheter having a terminal portion and distal tip that is placed in the vessel proximate the CTO by visualizing a radiopaque band positioned at the shared distal terminal portion of the first lumen and the second lumen. The radiopaque band is positionally referenced through various spectroscopic techniques, such as X-ray fluoroscopy, for example.

In yet another embodiment of the present invention, a dual lumen guidewire support catheter has lumens that have a very small crossing profile. In this embodiment, the dual lumen guidewire support catheter is an ultra-thin-walled exchange catheter generally having a lubricious coating inside the guidewire lumens and/or on the outside of the catheter, the lubricious coating being a hydrophilic, hydrophobic and/or other lubricious coating, thus increasing the usability of the dual lumen guidewire support catheter.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

As described herein, the dual lumen guidewire support catheter is employed in placing a guidewire within the lumen of a coronary artery and through a blockage such as a CTO within a coronary artery. However, this description is exemplary only, and it should be appreciated that embodiments of the present catheter can be employed for the piercing of a blockage in a variety of body lumens, including the urinary tract, bile duct, esophagus and tracheo-bronchial tree, neurovascular, peripheral vascular, cardiac, and renal catheters, among others.

A dual lumen guidewire support catheter as illustrated in FIGS. 1-5D are configured for intraluminal passage via a body vessel, and as such is sized for such passage, depending on the particular vessel dimensions. For example, for use in a coronary artery, the catheters can have an outside diameter of approximately 1.3 to 1.7 mm, with a range of about 0.5 mm to about 10 mm, and an inside diameter of approximately 0.8 to 1.2 mm, with a range of about 0.4 mm to about 9.9 mm, though these dimensions are merely exemplary. For example, the use of the catheter in non-coronary vessels may require catheter dimensions of a significantly larger scale than what would be required for a coronary artery. Though, as depicted in FIGS. 1 through 5D, the catheter is cylindrical, other cross sectional shapes can also define the catheter shape.

Figure 1A:
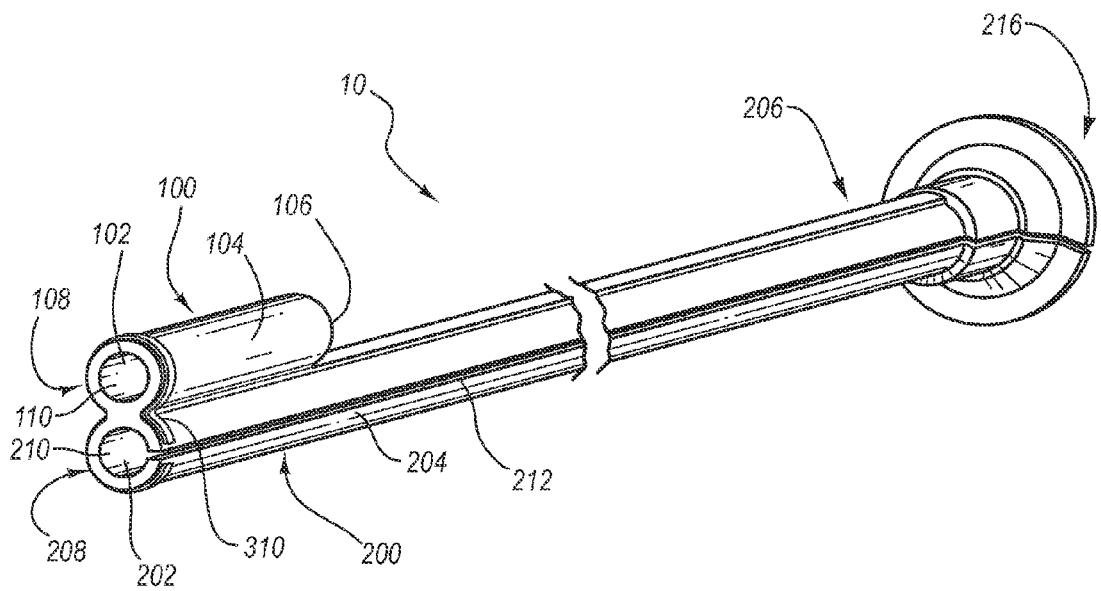
FIG. 1A is a side perspective view of a dual lumen guidewire support catheter depicting a first lumen having a rapid exchange conformation and a second lumen having an over the wire configuration with a discontinuity along the length of the second lumen.

FIGS. 1A through 4B depict various features of embodiments of the present invention. Turning to Figures 1A and 1B, which is generally directed to a catheter 10, the catheter 10A has a first lumen portion 100 and a second lumen portion 200. The first lumen portion 100 and the second lumen portion 200 are disposed one on top of the other. The first lumen portion 100, and so a first lumen 102 of the first lumen portion 100, extends along a portion of the second lumen portion 200, and so a second lumen 202 of the second lumen portion 200. The first lumen portion 100 may be from about 0.1% up to about 100% of the length of the second lumen portion 200, depending upon if the first lumen portion 100, and so the first lumen 102, is a rapid exchange portion or lumen or if both the first lumen portion 100 and the second lumen portion 200, and so the first lumen 102 and second lumen 202, are over the wire lumens. First lumen portion 100 and second lumen portion 200 share a common wall throughout a portion of their length. In one embodiment, first lumen portion 100 has a proximal end 106 that is axially staggered with respect to the common length shared by first lumen portion 100 and second lumen portion 200 and so axially staggered from a proximal end 206 and access port 216. First lumen portion 100 has a first lumen distal end 108 and second lumen portion 200 has a second lumen distal end 208. In an embodiment of catheter 10, first lumen distal end 108 and second lumen end 208 share the same terminal end.

First lumen portion 100 has a first lumen interior 110 and second lumen portion 200 has a second lumen interior 210 that can have a lubricious coating to further enable the passing of a guidewire, balloon catheter, stent or other intraluminally delivered device. First lumen portion 100 has a first lumen exterior 104 and second lumen portion 200 has a second lumen exterior 204, each of which may have a lubricious coating, such as but not limited to, a hydrophilic, hydrophobic, or other lubricious coating as known to those skilled in the art, thus facilitating the movement of catheter 10 throughout the vasculature of the patient without damaging the vessel interior.

Figure 1B:
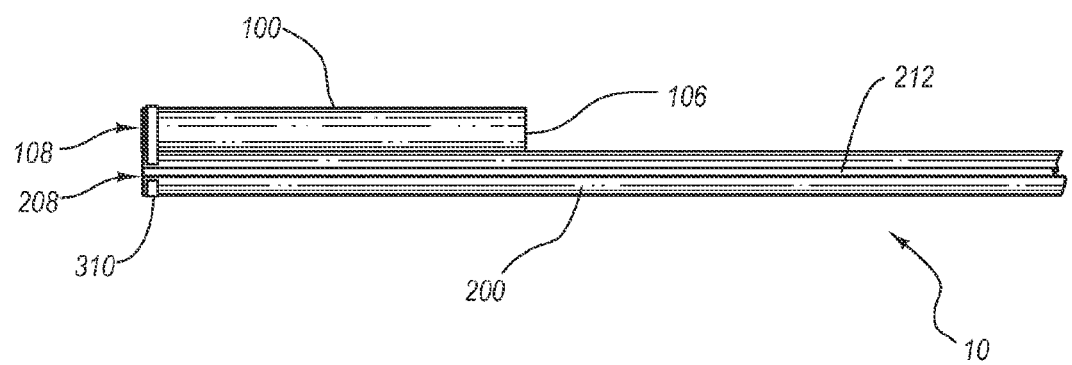
FIG. 1B is a perspective view of the dual lumen guidewire support catheter of FIG. 1 A further depicting a radiopaque band at the terminal, distal end.

In an embodiment of catheter 10, and with continued reference to FIGS. 1A and 1B, first lumen distal end 108 and second lumen distal end 208 have a position indicator. The position indicator is implemented as an annular, radiopaque ("RO") band 310 that is disposed about first lumen exterior 104 and second lumen exterior 204 at first lumen distal end 108 and at second lumen distal end 208. RO band 310 is composed at least partially of a radiopaque material, including metals such as platinum, gold, and alloys thereof, plastics, polymers, and other synthetic materials, etc. RO band 310 may or may not include discontinuities, depending on whether or not first lumen portion 100 and/or second lumen portion 200 contain any discontinuities.

Radiopaque band 310 is useful for the precise proximal placement of first and second lumen distal ends 108, 208 as they travel within a true lumen of vessel 300 as defined by a vessel interior 302, a vessel wall 304 and a vessel exterior 306, to the proximal side of occlusion 308. The position of radiopaque band 310 and therefore the position of first lumen distal end 108 and second lumen distal end 208 may be precisely determined through various radiographic techniques such as X-ray fluoroscopy.

Figure 2A:
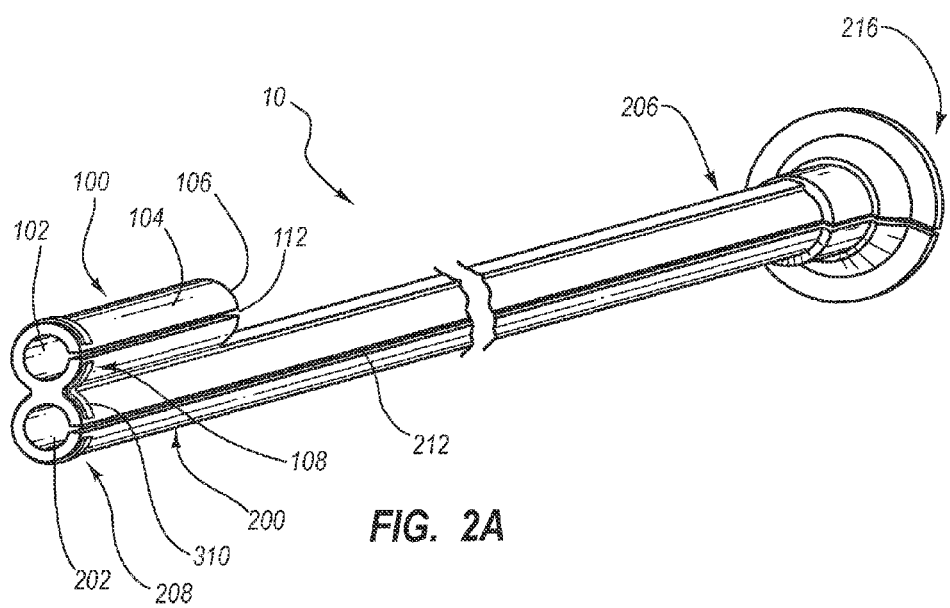
FIG. 2A is a side perspective view of a dual lumen guidewire support catheter depicting a first lumen having a rapid exchange conformation and a second lumen having an over the wire configuration, both lumens having a discontinuity along their lengths.

Turning to FIGS. 1A and 2A, depicted are perspective views of catheters 10 showing discontinuities in the first lumen portion 100 and/or the second lumen portion 200. As shown in FIG. 2A, the first lumen portion 100 includes a first lumen discontinuity 112 in first lumen portion 100 and a second lumen discontinuity 212 in second lumen portion 200. First lumen discontinuity 112 and second lumen discontinuity 212 are of a sufficient width such that a first guidewire 114 (FIGS. 5A-5D) or a second guidewire 214 (FIGS. 5A-5D) may be moved therethrough, respectively. For example, in an embodiment of catheter 10, first lumen discontinuity 112 and/or second lumen discontinuity 212 has an outer diameter that is from about 0.007" to about 0.040". Optionally, the first lumen discontinuity 112 and/or the second lumen discontinuity 212 is a weakened portion of the first lumen portion 100 and the second lumen portion 200 respectfully, this weakened portion splitting or separating as a physician or clinician pulls the guidewire outwardly from within the first lumen 102 or second lumen 202. Optionally, the lumen walls of the first lumen portion 100 and/or the second lumen portion 200 are flexible and capable of passing guidewires having outer diameters larger than the width of the discontinuity of the lumen walls. The guidewires can be composed of a suitable material, such as stainless steel, NiTiNOL, plastics, polymers, and suitable combinations of these materials, for instance.

Figure 2B:
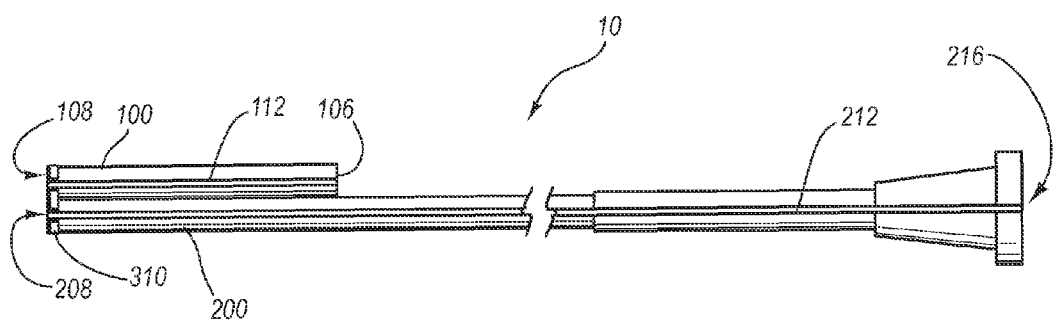
FIG. 2B is a perspective view of the dual lumen guidewire support catheter of FIG. 2A further depicting a radiopaque band at the terminal, distal end.

In the embodiment of catheter 10 depicted in FIGS. 1A-2B, first lumen portion 100 is a rapid exchange portion with a rapid exchange lumen and may or may not have a first lumen discontinuity 112; FIGS. 1A-1B illustrating the catheter 10 without the discontinuity, while FIGS. 2A-2B illustrate the catheter 10 with the discontinuity 112. In an embodiment of catheter 10, second lumen discontinuity 212 runs the entire length of second lumen portion 200, including radiopaque band 310, to the access port 216. The lumen walls may be made from materials such as polyethylene, polyimide, polyamide, polyvinylchloride, polyester and other high strength polymers such as polyetheretherketone, for example.

Catheter 10 is sized according to a particular need so as to both be able to travel intraluminally through a vessel true lumen to occlusion 308 where, if first guidewire 114 does not pass through occlusion 308, second guidewire 214 is to be deployed in order to cross occlusion 308 and to enable passage therethrough of a stent delivery catheter, balloon catheter, or other catheter device over second guidewire 214.

Having first lumen terminal distal end 108 and second lumen terminal distal end 208 positioned at the same axial position and sharing a terminal, distal end of catheter 10 is useful for accurately deploying a distal end of catheter 10 over a first guidewire 114 at the proximal side of occlusion 308, in body vessel 300. When the distal end of catheter 10 is placed proximal to occlusion 308, second guidewire 214 may then be advanced through second lumen portion 200. Since first guidewire 114 and second guidewire 214 occupy different planes within vessel 300, the chance of second guidewire 214 finding the same false lumen as first guidewire 114 is substantially reduced. When guidewire 214 reaches the distal end of catheter 10, second guidewire 214 is advantageously positioned to pierce through occlusion 308 because second guidewire 214 is straight and its pushability is therefore substantially increased versus a wire that is not receiving support along its length from second lumen portion 200, and first lumen portion 100 of catheter 10.

Together with FIGS. 1A through 2B, reference is now made to FIGS. 3A-4B, which show various configurations of catheter 10. Catheter 10 may be configured such that first lumen portion 100 and second lumen portion 200 have an over the wire configuration or a rapid exchange configuration. Embodiments of catheter 10 having various configurations consisting of either rapid exchange, or over the wire allows catheter 10 to be used in a variety of different situations depending upon the application needed, the type of guidewire required and/or other devices that need to be delivered intraluminally. Accordingly, first lumen portion 100 may be configured as a rapid exchange lumen or as an over the wire lumen and may or may not have a lumen wall discontinuity.

As depicted in FIGS. 2A and 2B, an embodiment of catheter 10 may have first lumen portion 100 as a rapid exchange lumen and second lumen portion 200 also as an over the wire lumen, both first lumen portion 100 and second lumen portion 200 having a discontinuity along their entire length.

Figure 3A:
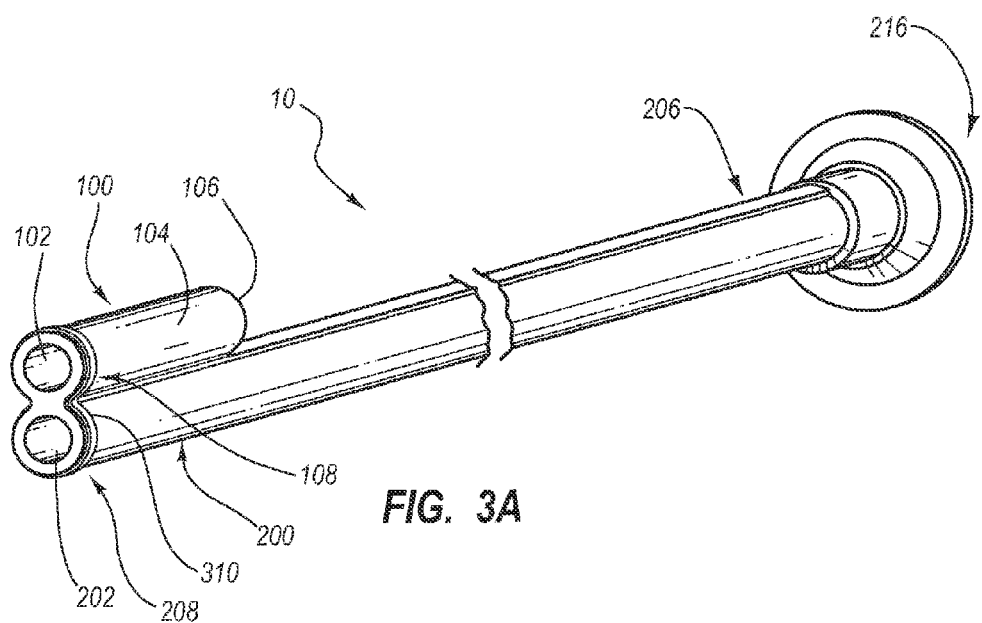
FIG. 3A is a side perspective view of a dual lumen guidewire support catheter depicting a first lumen having a rapid exchange conformation and a second lumen having an over the wire configuration, neither lumen having a discontinuity.
Figure 3B:
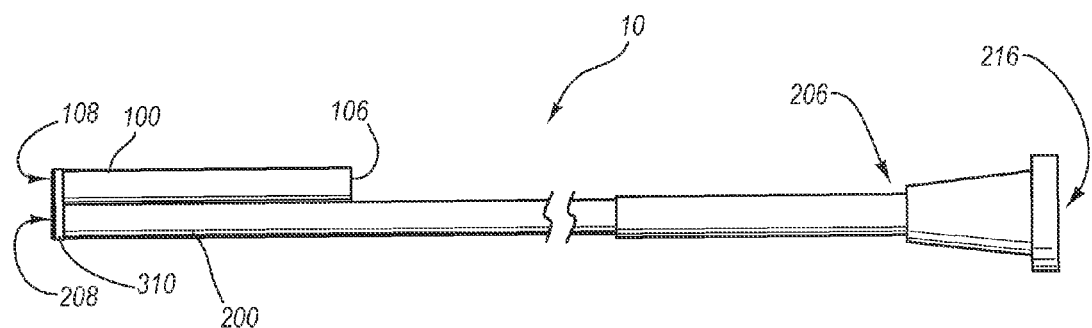
FIG. 3B is a perspective view of the dual lumen guidewire support catheter of FIG. 3A further depicting a radiopaque band at the terminal, distal end.

As depicted in FIGS. 3A and 3B, an embodiment of catheter 10 may have first lumen portion 100 as a rapid exchange lumen and second lumen portion 200 as an over the wire lumen, neither first lumen portion 100 or second lumen portion 200 having a discontinuity along their entire length.

Figure 4A:
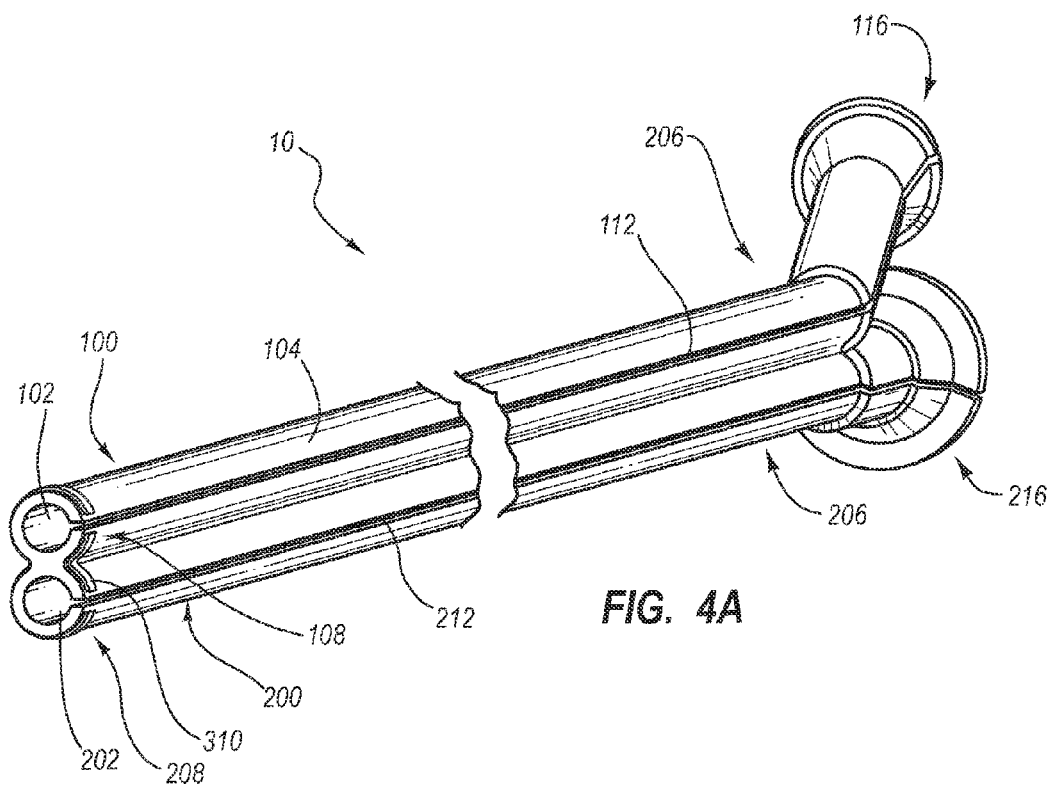
FIG. 4A is a side perspective view of a dual lumen guidewire support catheter depicting a first lumen having an over the wire conformation and a second lumen having an over the wire configuration, both lumens having a discontinuity along their lengths.
Figure 4B:
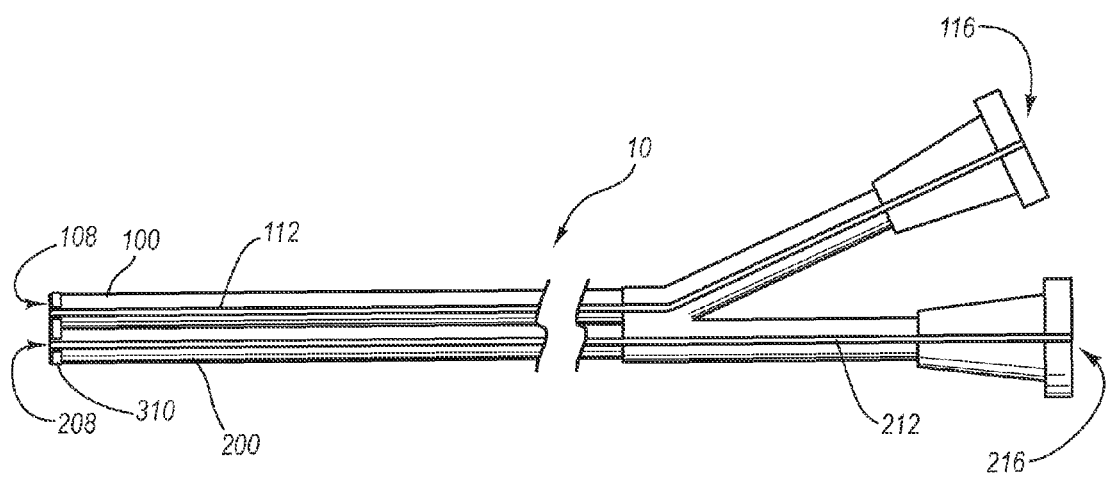
FIG. 4B is a perspective view of the dual lumen guidewire support catheter of FIG. 4A further depicting a radiopaque band at the terminal, distal end.

As depicted in FIGS. 4A and 4B, an embodiment of catheter 10 may have first lumen portion 100 as an over the wire lumen and second lumen portion 200 as an over the wire lumen, both with a discontinuity along their respective entire lengths to the access ports 116 and 216.

Figure 5A:
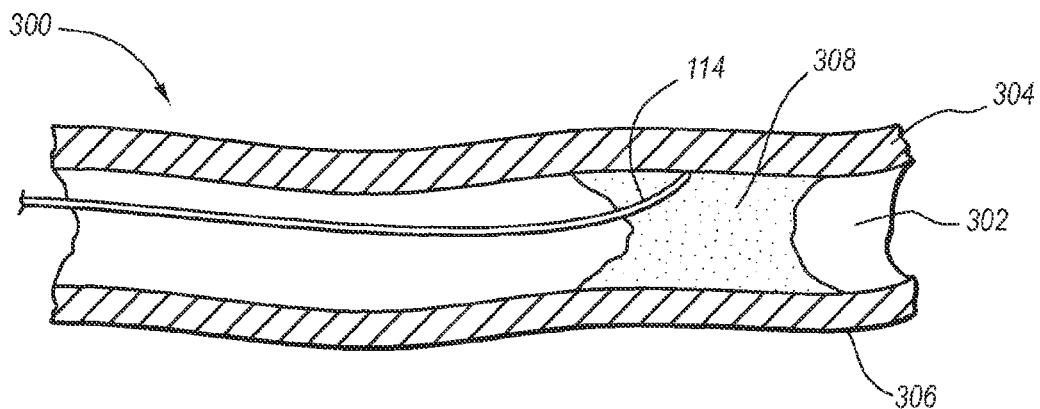
FIGS. 5A, 5B, 5C and 5D are cross sectional views of a body vessel depicting the method of use of the dual lumen guidewire support catheter of FIG. 1A and FIG. 1B to pierce a chronic total occlusion with a second guidewire.
Figure 5B:
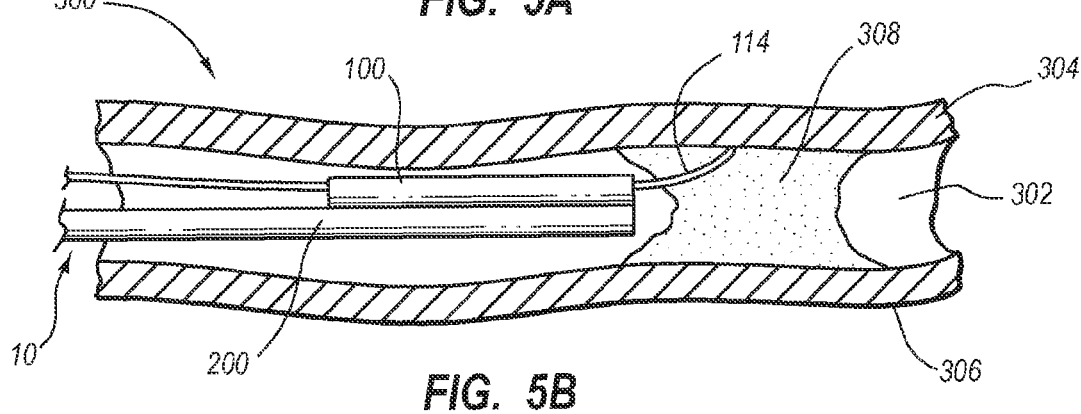
Figure 5C:
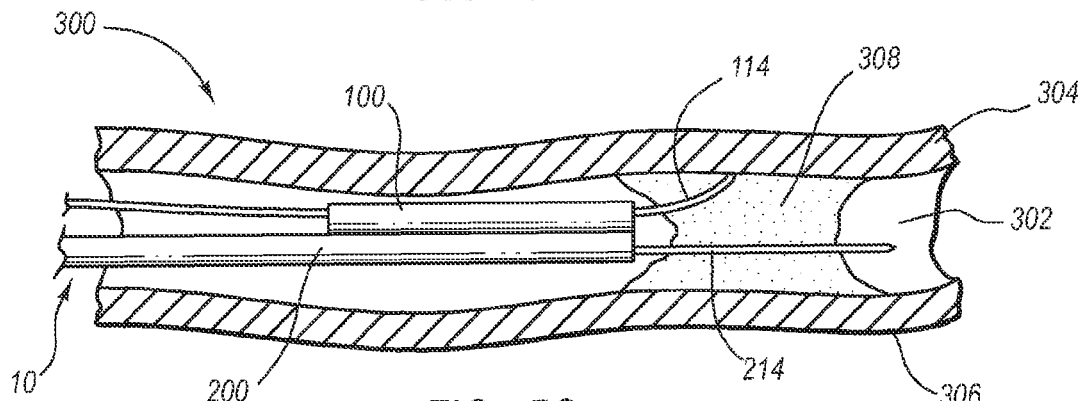
Figure 5D:
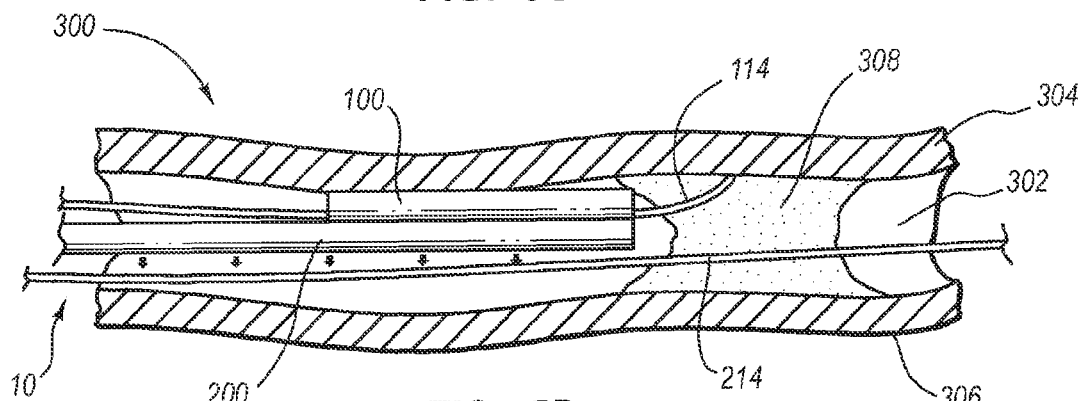

FIGS. 5A, 5B, 5C and 5D depict a method of using an embodiment of catheter 10 to pierce a blockage in a vessel. The blockage may be a thrombus, plaque, lesion, chronic total occlusion or any other blockage within a vessel. As depicted in FIG. 5A, a first attempt at crossing a CTO is made using first guidewire 114, often first guidewire 114 gets stuck in occlusion 308, off-track or otherwise diverted into a false lumen, or other unproductive path such as passing through vessel interior 302, through vessel wall 304, and through vessel exterior 306 into a sub-intimal plane. As depicted in FIG. 5B, catheter 10 is then guided along first guidewire 114 until the distal end of catheter 10 is in place proximally to occlusion 308. As depicted in FIG. 5C, second guidewire 214 is then passed through second lumen portion 200 until it emerges into vessel 300 at a location proximal to occlusion 308. Being substantially supported by first lumen portion 100, second lumen portion 200 and generally by catheter 10, second guidewire 214 is then pierced through occlusion 308 until it is on the distal side of occlusion 308. As depicted in FIG. 5D, second guidewire 214 may then be displaced through second lumen discontinuity 212, such that catheter 10 is selectively coupled with only first guidewire 114. First guidewire 114 and catheter 10 may then be removed from vessel 300.

Using second guidewire 214 as a guide, a balloon catheter, stent or other device may be advanced over, or in connection with, second guidewire 214 until the balloon catheter or other device is displaced through occlusion 308. The balloon catheter may then be inflated and thus destroy the integrity of occlusion 308, for example. Second guidewire 214 may then be removed from the patient. Other embodiments of a method for treating a CTO or like vessel occlusion may be performed using the other above-mentioned embodiments of catheter 10.

Another advantage of the present invention is the ability of an operator of catheter 10 to use a rapid exchange length guidewire in an over the wire fashion that enables single operator use.

The present invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A dual lumen support catheter comprising:
   a first cylindrical portion having a first lumen and a first length; and
   a second cylindrical portion having a second lumen and a second length longer than or equal to said first length, said second cylindrical portion and said first cylindrical portion being laterally disposed one on top of another in a figure-eight configuration with the first and second cylindrical portions sharing a common wall throughout their joined length with each terminating at a common distal end and each terminating at a separate proximal terminal end, said second cylindrical portion having a second discontinuity extending from the common distal end to the proximal end of said second cylindrical portion, the second discontinuity being a continuous slit, the first cylindrical portion having a first discontinuity extending from the common distal end to the proximal end of said first cylindrical portion, the first and second cylindrical portions forming a structure that includes first and second guidewire passageways having the first and second discontinuities.

2. The dual lumen support catheter of claim 1, wherein said first cylindrical portion is a rapid exchange lumen portion and said second cylindrical portion is an over the wire lumen portion.

3. The dual lumen support catheter of claim 1, wherein each of said first cylindrical portion and said second cylindrical portion is an over the wire portion.

4. The dual lumen support catheter of claim 3, said first cylindrical portion and said second cylindrical portion having the first and second discontinuities in their walls comprising continuous slits from each of their proximal ends to the common distal end, with the first discontinuity being disposed on a first side of the first cylindrical portion and the second discontinuity being disposed on a second side of the second cylindrical portion relative to the shared common wall.

5. The dual lumen support catheter of claim 4, wherein said first and second discontinuities are capable of passing a guidewire therethrough.

6. The dual lumen support catheter of claim 1, further comprising a radiopaque position indicator.

7. The dual lumen support catheter of claim 1 comprising at least one port in a lateral surface of a proximal terminal portion of said dual lumen support catheter.

8. A dual lumen support catheter comprising:
   a first cylindrical portion having a first interior surface defining a first lumen, a first length, and a first exterior surface, said first interior surface having a lubricious coating and said first exterior surface having a lubricious coating; and
   a second cylindrical portion having a second interior surface defining a second lumen, a second length longer than or equal to said first length, and a second exterior surface, said second interior surface having a lubricious coating and said second exterior surface having a lubricious coating;
   said second cylindrical portion and said first cylindrical portion being laterally disposed one on top of another in a figure-eight configuration with the first and second cylindrical portions each sharing a common wall throughout their joined length and with each terminating at a common distal end, wherein the figure-eight configuration is defined by the first exterior surface having a first cross-sectional dimension, the second exterior surface having a second cross-sectional dimension, and the common wall having an exterior surface region defined by first and second longitudinal channels between the first and second cylindrical portions that curve inward from the first and second cylindrical portions to define a third cross-sectional dimension that is less than the first and second cross-sectional dimensions;
   said second cylindrical portion having a second discontinuity extending from the common distal end toward a proximal end of said second cylindrical portion with the second discontinuity being disposed on a second side of the second cylindrical portion relative to the shared common wall, the second discontinuity being a continuous slit, the first cylindrical portion having a first discontinuity extending from the common distal end to a proximal end of said first cylindrical portion with the first discontinuity being disposed on a first side of the first cylindrical portion relative to the shared common wall, the first and second cylindrical portions forming a structure that includes first and second guidewire passageways having the first and second discontinuities.

9. The dual lumen support catheter of claim 8, wherein said first cylindrical portion is a rapid exchange lumen portion and said second cylindrical portion is an over the wire lumen portion.

10. The dual lumen support catheter of claim 9, wherein said first discontinuity or said second discontinuity is capable of passing a guidewire therethrough.

11. The dual lumen support catheter of claim 9, wherein said second cylindrical portion comprises another discontinuity.

12. The dual lumen support catheter of claim 11, wherein each of said first discontinuity or said second discontinuity and said another discontinuity is capable of passing a guidewire therethrough.

13. The dual lumen support catheter of claim 8, wherein each of said first cylindrical portion and said second cylindrical portion is an over the wire portion.

14. The dual lumen support catheter of claim 8, wherein said first and second discontinuities are capable of passing a guidewire therethrough.

15. The dual lumen support catheter of claim 8, further comprising a radiopaque position indicator.

16. The dual lumen support catheter of claim 8, comprising at least one port in a lateral surface of a proximal terminal portion of said dual lumen support catheter.

17. A dual lumen support catheter, comprising:

a first cylindrical portion and a second cylindrical portion each having a separate proximal terminal end with the proximal terminal end of the first cylindrical portion being separated from the proximal terminal end of the second cylindrical portion and a distal terminal end defining a common distal terminal portion for placement in a vessel proximal to a chronic total occlusion of said vessel;

each of said first cylindrical portion and said second cylindrical portion including a continuous slit extending from their distal terminal ends to their proximal terminal ends, respectively;

said first cylindrical portion and said second cylindrical portion being laterally disposed one on top of another in a figure-eight configuration with the first and second cylindrical portions each sharing a common wall throughout their joined length, with the first slit being disposed on a first side of the first cylindrical portion and the second slit being disposed on a second side of the second cylindrical portion relative to the shared common wall, wherein the figure-eight configuration is defined by the first cylindrical portion having a first cross-sectional dimension, the second cylindrical portion having a second cross-sectional dimension, and the common wall having an exterior surface region defined by first and second longitudinal channels between the first and second cylindrical portions that curve inward from the first and second cylindrical portions to define a third cross-sectional dimension that is less than the first and second cross-sectional dimensions;

a port defined in a lateral surface of a terminal proximal portion of the catheter defined by the proximal terminal ends, said port being sized so as to allow passage therethrough of a stent delivery catheter, balloon catheter or guidewire into the vessel; and a radiopaque marker positioned at a distal terminal end of said catheter.

18. The catheter as defined in claim 17, wherein said port is in communication with a lumen of the catheter, and wherein a second guidewire is configured to track via a second lumen of the catheter.

* * * * *